(12) United States Patent
Stolka et al.

(10) Patent No.: US 10,284,762 B2
(45) Date of Patent: May 7, 2019

(54) SYSTEM AND METHOD FOR TARGETING FEEDBACK

(71) Applicant: Clear Guide Medical, Inc., Baltimore, MD (US)

(72) Inventors: Philipp Jakob Stolka, Baltimore, MD (US); Pezhman Foroughi, Cockeysville, MD (US); Matthew C. Rendina, Baltimore, MD (US); Gregory Donald Hager, Baltimore, MD (US); Allison Mariko Okamura, Mountain View, CA (US)

(73) Assignees: Clear Guide Medical, Inc., Baltimore, MD (US); The Board of Trustees of the Leland Stanford Junior University, Stanford, CA (US)

( * ) Notice: Subject to any disclaimer, the term of this patent is extended or adjusted under 35 U.S.C. 154(b) by 538 days.

(21) Appl. No.: 14/524,570

(22) Filed: Oct. 27, 2014

(65) Prior Publication Data
US 2016/0119529 A1    Apr. 28, 2016

(51) Int. Cl.
*A61B 8/00*    (2006.01)
*A61B 8/08*    (2006.01)
(Continued)

(52) U.S. Cl.
CPC ....... *H04N 5/23203* (2013.01); *A61B 8/0841* (2013.01); *A61B 8/4444* (2013.01);
(Continued)

(58) Field of Classification Search
None
See application file for complete search history.

(56) References Cited

U.S. PATENT DOCUMENTS

| 7,686,740 B1 | 3/2010 | Chang | |
|---|---|---|---|
| 2006/0087746 A1* | 4/2006 | Lipow | A61B 34/70 359/689 |

(Continued)

OTHER PUBLICATIONS

Kadleček, P., Kmoch, P., & Křivánek, J. (Jun. 2014). Haptic rendering for under-actuated 6/3-DOF haptic devices. In International Conference on Human Haptic Sensing and Touch Enabled Computer Applications (pp. 63-71). Springer Berlin Heidelberg.*

(Continued)

*Primary Examiner* — Carolyn A Pehlke
(74) *Attorney, Agent, or Firm* — Venable LLP; Henry J. Daley

(57) ABSTRACT

A system for guidance of an imaging device may include a handheld imaging device, a multidirectional feedback device, and a control unit in communication with the multidirectional feedback device and the handheld imaging device. The control unit may be configured to receive a target location, determine an initial position and pose of the handheld imaging device, calculate a position and pose deviation relative to said initial position and pose, translate said position and pose deviation into control data, and transmit said control data to the multidirectional feedback device, wherein the multidirectional feedback device uses control data to provide an operator with feedback to guide the handheld imaging device towards the target.

30 Claims, 12 Drawing Sheets

(51) Int. Cl.
*G06F 3/01* (2006.01)
*A61B 34/00* (2016.01)
*G06F 9/451* (2018.01)
*H04N 5/232* (2006.01)
*G06F 3/0346* (2013.01)

(52) U.S. Cl.
CPC ............... *A61B 8/46* (2013.01); *A61B 8/466* (2013.01); *A61B 8/52* (2013.01); *A61B 8/54* (2013.01); *A61B 34/76* (2016.02); *A61B 34/77* (2016.02); *G06F 3/016* (2013.01); *G06F 3/0346* (2013.01); *G06F 9/453* (2018.02); *H04N 5/23293* (2013.01); *A61B 8/464* (2013.01)

(56) References Cited

U.S. PATENT DOCUMENTS

| | | |
|---|---|---|
| 2007/0142751 A1 | 6/2007 | Kang et al. |
| 2008/0208006 A1 | 8/2008 | Farr |
| 2010/0073150 A1 | 3/2010 | Olson et al. |
| 2012/0101388 A1 | 4/2012 | Tripathi |
| 2012/0232780 A1 | 9/2012 | Delson et al. |
| 2013/0016185 A1 | 1/2013 | Stolka et al. |
| 2013/0218024 A1* | 8/2013 | Boctor .................. A61B 34/20 600/476 |
| 2014/0114193 A1 | 4/2014 | Anthony et al. |
| 2014/0243658 A1 | 8/2014 | Breisacher et al. |

OTHER PUBLICATIONS

PCT International Search Report and Written Opinion dated Jan. 14, 2016 in corresponding application PCT/US2015/57560.

Stolka et al., "Multi-DoF probe trajectory reconstruction with local sensors for 2D-to-3D ultrasound," International Symposium on Biomedical Imaging: From Nano to Macro, 2010, pp. 316-319.

Stolka et al., "Navigation with local sensors in handheld 3d ultrasound: initial in-vivo experience," SPIE Medical Imaging 2011, pp. 79681J-79681J.

Wang et al., "The Kinect as an Interventional Tracking System," SPIE Medical Imaging, 2012, pp. 93160U-83160U.

* cited by examiner

SYSTEM AND METHOD FOR TARGETING FEEDBACK

BACKGROUND

1. Field of Invention

The field of the currently claimed embodiments of this invention relate to targeted feedback, and more particularly to targeted feedback for imaging devices with one or more sensors for observation and tracking of one or more tools.

2. Discussion of Related Art

In image-guided interventions, the tracking and localization of imaging devices and medical tools during procedures are considered the main enabling technology in image-guided surgery (IGS) systems.

Limitations of the current approach on both the research and commercial sides may be attributed to the available tracking technologies and to the feasibility of integrating these systems and using them in clinical environments. Thus, there remains a need for improved imaging devices for use in image-guided surgery.

SUMMARY

Aspects of the invention may involve systems, devices, and methods. In one embodiment, a system for guidance of an imaging device may be provided. The system may include a handheld imaging device; a multidirectional feedback device (e.g., an ungrounded haptic feedback device, an audio feedback device, and/or a visual feedback device); and a control unit in communication with the multidirectional feedback device and the handheld imaging device The control unit may be configured to: receive a target location, determine an initial position and pose of the handheld imaging device, calculate a position and pose deviation relative to said initial position and pose, translate said position and pose deviation into control data, and transmit said control data to the multidirectional feedback device, wherein the multidirectional feedback device uses said control data to provide an operator with feedback to guide the handheld imaging device towards the target.

In another embodiment a method of guidance of a handheld imaging device may be provided. The method may include receiving by a control unit a target location; determining by the control unit an initial position and pose of the handheld imaging device; calculating by the control unit a position and pose deviation relative to said initial position and pose; translating by the control unit said position and pose deviation into feedback instructions; and transmitting by the control unit said feedback instructions to a multidirectional feedback device, wherein the multidirectional feedback device uses the feedback instructions to instruct an operator to guide the handheld imaging device toward the target.

BRIEF DESCRIPTION OF THE DRAWINGS

Further objectives and advantages will become apparent from a consideration of the description, drawings, and examples.

DETAILED DESCRIPTION

Figure 1:
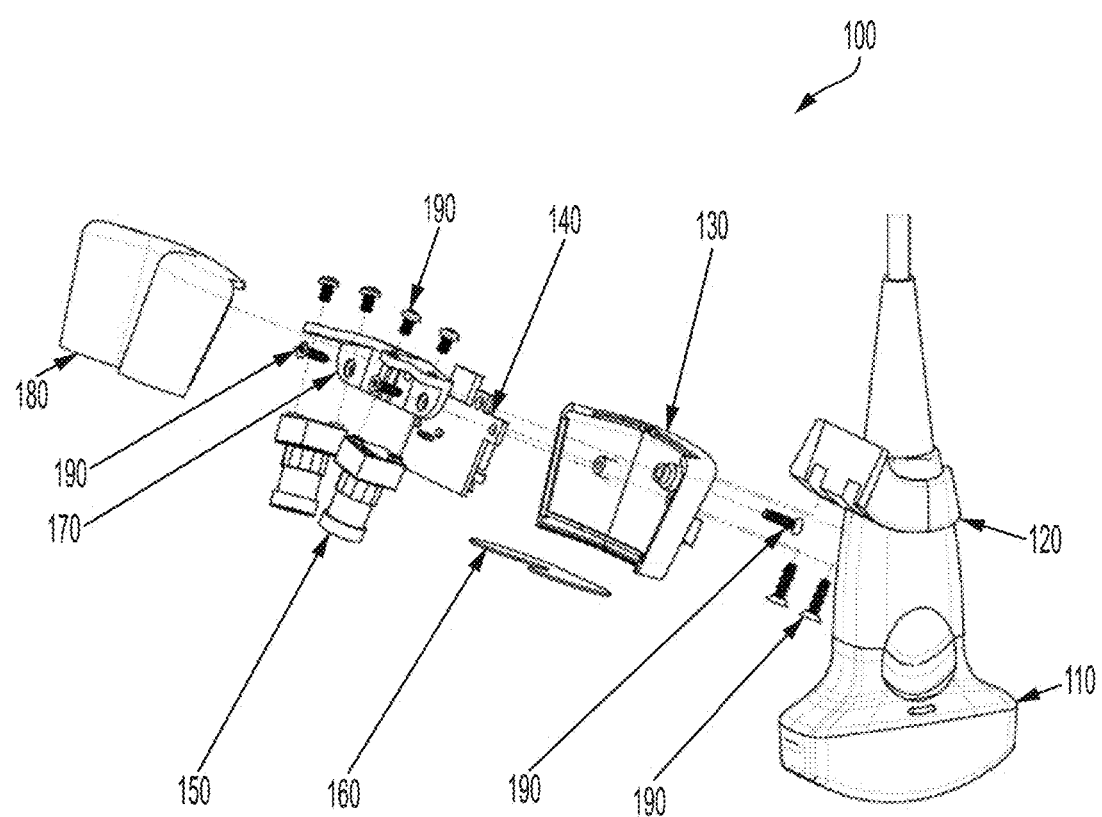
FIG. 1 shows an example imaging component for an example imaging system.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Some embodiments of this invention describe IGI-(image-guided interventions)-enabling "platform technology" going beyond the current paradigm of relatively narrow image-guidance and tracking. It simultaneously aims to overcome limitations of tracking, visualization, and guidance; specifically using and integrating techniques e.g. related to needle identification and tracking using 3D computer vision and structured light; and imaging device tracking using local sensing approaches; among others. Examples of IGI may be seen in U.S. patent application Ser. No. 13/511,101, titled "Low-cost image-guided navigation and intervention systems using cooperative sets of local sensors," published as U.S. Patent Application Publication No. 2013/0016185. Furthermore U.S. patent application Ser. Nos. 14/092,843 and 14/092,755 depict sample IGIs. The contents of U.S. patent application Ser. Nos. 13/511,101, 14/092,843, and 14/092,755 are incorporated herein by reference in their entirety.

The current invention covers a wide range of different embodiments, sharing a tightly integrated common core of components and methods used for general imaging, projection, vision, targeting, and local sensing.

Some embodiments of the current invention are directed to combining a group of complementary technologies to provide a local sensing approach that can provide enabling technology for the tracking of targets and guidance of medical devices or tools, for example, with the potential to significantly reduce errors and increase positive patient outcomes. This approach can provide a platform technology for the tracking (e.g., ultrasound probes, the patient, the environment, and/or other imaging devices), intervention guidance, and/or information visualization according to some embodiments of the current invention. By combining ultrasound imaging with image analysis algorithms and probe-mounted light-sensitive devices, feedback devices, independent optical-inertial sensors, according to some embodiments of the current invention, it is possible to reconstruct the position and trajectory of surgical needles and other tools or objects by incrementally tracking and guiding their current motion.

Some embodiments of the current invention allow the segmentation, tracking, and guidance of needles, imaging devices (e.g., ultrasound probes) and other tools, using visual, ultrasound, and/or other imaging and localization modalities and haptic, audio and/or visual feedback.

Such devices can allow imaging procedures with improved sensitivity and specificity as compared to the current state of the art. This can open up several possible application scenarios that previously required harmful X-ray/CT or expensive MRI imaging, and/or external tracking, and/or expensive, imprecise, time-consuming, or impractical hardware setups, or that were simply afflicted with an inherent lack of precision and guarantee of success, such as: biopsies, RF/HIFU ablations etc.: can allow 2D- or 3D-ultrasound-based needle guidance, brachytherapy: can allow 3D-ultrasound acquisition and needle guidance for precise brachytherapy seed placement, other applications relying on tracked imaging and tracked tools.

Some embodiments of the current invention may provide several advantages over existing technologies, such as combinations of: low-cost tracking, local, compact, and non-intrusive solution—ideal tracking system for hand-held and compact ultrasound systems that are primarily used in intervention and point-of-care clinical suites, but also for general needle/tool tracking under visual tracking in other interventional settings.

For example, some embodiments of the current invention are directed to system and methods to guide an imaging device and/or medical tool. This guidance may be combined with techniques for the tracking of imaging devices (e.g., ultrasound probes) and/or medical tools (e.g., needles, pointers, biopsy tools, laparoscopes, ablation devices, surgical instruments, or elongated tools). By combining ultrasound imaging with image analysis algorithms and probe-mounted light-sensitive devices it is possible to reconstruct the position and trajectory of tools (e.g., needles, pointers, biopsy tools, laparoscopes, ablation devices, surgical instruments, or elongated tools) and other objects by incrementally tracking their current motion according to an embodiment of the current invention. This can provide several possible application scenarios that previously required expensive, imprecise, or impractical hardware setups. For example, 3D ultrasound-based needle guidance.

Current sonographic procedures mostly use handheld 2D ultrasound (US) probes that return planar image slices through the scanned 3D volume (the "region of interest" (ROI)). For percutaneous interventions requiring tool guidance, prediction of the tool trajectory is currently based on tracking with sensors attached to the distal (external) tool end and on mental extrapolation of the trajectory, relying on the operator's experience. An integrated system with 3D ultrasound, tool tracking, tool trajectory prediction and interactive user guidance would be highly beneficial.

In one embodiment, a handheld device may contain a feedback system (e.g., haptic, audio, and/or visual) used to assist an operator in targeting. The handheld device may also enable position sensing. The feedback system may assist an operator in positioning a tool to or near a target. The feedback system may assist an operator in keeping an imaging device (e.g., an ultrasound probe) located at or above a target. For example, the feedback system may direct the operator to keep the imaging device at a viewing location for positioning a medical device (e.g., a needle) to a target. A control unit may determine an initial position and pose for an imaging device. The control unit may then determine if the imaging device is moving in the wrong direction (e.g., the operator of the imaging device is inadvertently sliding and/or rotating away from the region of interest) and/or if the imaging device is not or not quickly enough moving towards a target area. If the imaging device is not conforming to the target area, the control unit may transmit operator feedback to instruct the operator to move in a particular direction.

The feedback system may provide for spatial targeting enhancement when using a medical visualization/imaging system. The feedback system may include a directional haptic feedback device for handheld use (e.g., ungrounded haptic feedback device) and a control unit for calculation of targeting information and resulting feedback control data. An embodiment may also include directional audio or visual feedback devices. In one embodiment a feedback device may contain any combination of haptic, audio, and/or visual feedback to the operator.

The haptic feedback device may include actuators for vibrotactile feedback, torque feedback, or both. The actuators may be designed and arranged in such a way as to enable transmission of directional haptic information ("haptic display") to the operator to provide instruction on positioning the device relative to some other object (e.g., external target locations or instrument positions).

The visual feedback may include arrows or animations on a screen. The audio feedback may include different tones and/or varying pitch to direct the operator to bring the imaging device or a medical tool to a determined location.

The feedback system may include a control unit that receives a target location relative to the device pose, or an instrument location relative to said target location, and computes the resulting device pose deviation. This pose deviation may be translated into haptic display actuations, audio feedback, and/or visual feedback. The haptic display actuations may include torque impulses for rotational deviation (e.g., generated by one or more asymmetrical-impulse-driven flywheels oriented so as to be linearly independent), vibrotactile impulses for translational deviation (e.g., generated by one or more asymmetric vibration actuators oriented so as to be linearly independent), or both. Depending on the application requirements, subsets of the full six degrees of freedom for haptic feedback may be realized in the device. The operator can then use the displayed directional information to position the haptic device in an ideal position that minimizes the device pose deviation in a closed-loop control fashion.

In one embodiment, the haptic feedback device may be mounted on a handheld ultrasound probe. Feedback actuations will thus result in, for example, haptic display that is directly calibrated to the operator's hand and the probe orientation. In another embodiment, the feedback device may be integrated into the handheld imaging device enclosure during manufacturing of the imaging device.

The haptic feedback device may contain sensing elements including one or more of accelerometers, gyroscopes, magnetometers, or optical sensors that provide pose and position information of the feedback device. In one embodiment, the haptic feedback device may be physically separate from the imaging device and the sensing elements may provide relative pose between the feedback device and the imaging device. The relative pose will transform the original pose deviation to feedback device coordinates, which then drives, for example, the haptic actuators. Such a physically separated haptic feedback device may be housed in, for example, a wrist-worn (e.g., a smartwatch), finger-worn, or forehead-worn housing, or otherwise strapped onto a body part of an operator. The sensing elements may also be contained in a haptic feedback device mounted on an imaging device.

In another embodiment, the feedback device can be mounted on an instrument to provide feedback (e.g., haptic, audio, and/or visual) to the operator. In one embodiment, one hand of the operator may be operating the imaging device and the other hand may be guiding an instrument, the feedback may assist the operator in guiding and/or placing the instrument relative to the imaging device or another external structure. For example, an operator may be operating an ultrasound probe to view images of a patient while receiving feedback on the placement of a needle to a target inside the patient.

In another application, the haptic feedback can be used to continuously position the imaging device along, for example, a time-varying path. The feedback may instruct an operator to move the imaging device, for example, back and forth over an area of the patient. Multiple images at slightly different angles will be acquired with the back and forth motion of the imaging device. These multiple images may be combined to produce a higher-dimensional image of the target area (e.g., a three-dimensional volume). Images may be acquired to produce a higher-dimensional image of the target area, for example, by placing the imaging device in a reference position, and then having the control unit issue vibrational feedback commands to the haptic feedback component that instruct the operator to translate the imaging device in the indicated direction until feedback ceases, or until feedback commands in a different direction are issued. In another example, the control unit may issue torque feedback commands to the haptic feedback component that instruct the operator to rotate the imaging device in the indicated direction until feedback ceases, or until feedback commands in a different direction are issued. Another example would perform the same functions based on visual or auditory feedback, using at least one of displayed directional indicators, displayed targeting indicators, audible directional indicators, and/or voice/speech samples. The auditory and visual feedback may be in addition to or replace the haptic feedback commands. Another example may estimate the imaging device position from the sensing elements included in the feedback device. During translations and rotations of the imaging device, imaging data may be collected and compounded into a higher-dimensional representation. One example of this technique may be found in "Multi-DoF probe trajectory reconstruction with local sensors for 2D-to-3D ultrasound", Stolka et al., ISBI 2010, incorporated herein by reference in its entirety. Instrument tracking capabilities, such as those described in "The Kinect as an Interventional Tracking System", Wang et al., SPIE 2012 (incorporated herein by reference in its entirety) may be used to dynamically navigate through the reconstructed three-dimensional image of the area by, for example, reslicing along a plane defined by the instrument.

FIG. 1 shows an embodiment of an imaging component 100 for an imaging system according to an embodiment of the current invention. Imaging component 100 includes an imaging device 110, bracket 120 that is structured to be attachable to imaging device 110. In the example of FIG. 1, the imaging device 110 is an ultrasound probe and bracket 120 is structured to be attached to a probe handle of the ultrasound probe. Ultrasound probes may include, for example, Ultrasonix #C5-2. However, the broad concepts of the current invention are not limited to only this example. The bracket 120 can be structured to be attachable to other handheld instruments for image-guided surgery, such as surgical orthopedic power tools or stand-alone handheld brackets, for example. In other embodiments, the bracket 120 can be structured to be attachable to the C-arm of an X-ray system or an MRI system, for example.

Imaging component 100 may include top shell 180 and bottom shell 130 that may be coupled together to form a head shell. Top shell 180 and bottom shell 130 may be coupled securely to stabilization assembly 170 (e.g., stabilization bar). Head shell may house stabilization assembly 170 and other components of imaging component 100. Screws 190 may be used to couple the components of imaging component 100.

In one embodiment, head shell may also include a feedback device. The feedback device may be a haptic feedback device including, for example, one or more linearly independent asymmetrical-impulse-driven flywheels and/or one or more linearly independent asymmetric vibration actuators. Visual feedback may be shown on display 220 and may include, for example, arrows or on-screen animations. In another embodiment, one or more indicator LEDs may be used to provide visual feedback. Audio feedback may be provided through the use of, for example, one or more speakers. The speakers may be located, for example, with the control unit.

In another embodiment, the feedback device may be separate from the head shell. The feedback device may be coupled to bracket 120 or may be removeably coupled to the imaging device through a separate fastener.

Imaging component 100 may also include one or more light-sensitive devices 150 (e.g., cameras, PSDs (position-sensitive devices), reflection-based laser sensing, etc.) securely attached to stabilization assembly 170. The one or more light-sensitive devices 150 may be at least one of a visible-light camera, an infra-red camera, a time-of-flight camera, a PSD (position-sensitive device), and/or a reflection-based laser sensing device in some embodiments of the current invention. The one or more light-sensitive devices 150 may be arranged to observe a surface region close to and during operation of the imaging component 100. In FIG. 1, the one or more light-sensitive devices 150 may be arranged and configured for stereo observation of a region of interest.

Imaging component 100 may also include a printed circuit board 140 that may include one or more microprocessors, one or more light sources, and a memory device. The light sources may include one or more LEDs, CFLs (compact fluorescent lamp), incandescent bulbs, and/or lasers. The light source may emit light in the visible spectrum, infrared, ultraviolet, and/or other spectrum. The printed circuit board may also be connected to one or more light-sensitive devices 150, the light source, and the memory device, and may be securely coupled to stabilization assembly 170.

Imaging component 100 may also include lens 160 that provides a screen for one or more light-sensitive devices 150. In one embodiment, lens 160 may be made of ultra-tough gorilla glass of 0.031" thickness. Lens 160 may be frosted or partially frosted to diffuse the light emitted from the light source.

Figure 2:
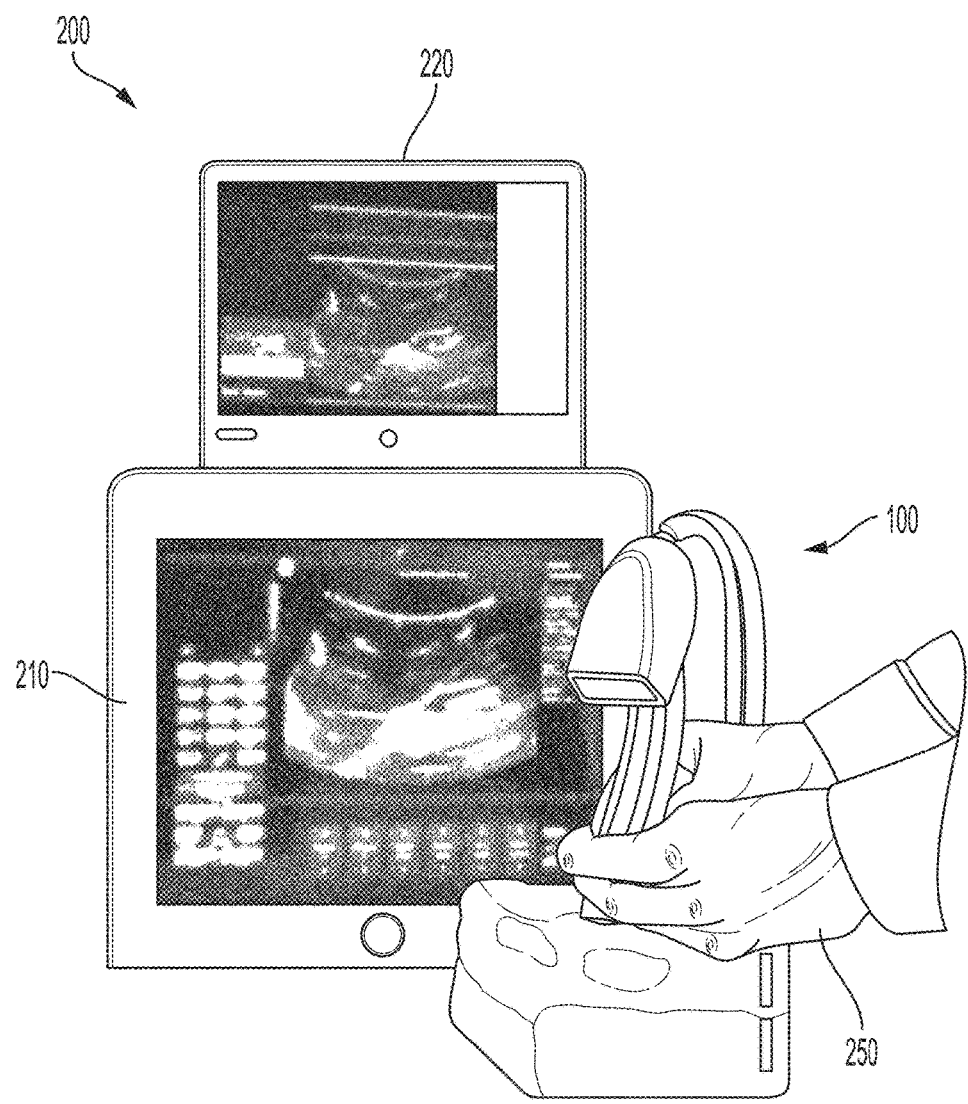
FIG. 2 shows another example imaging system.

FIG. 2 shows an embodiment of imaging system 200 according to an embodiment of the current invention. Imaging system 200 includes imaging component 100 being controlled by a user. The user is also inserting a tool. Imaging system 200 includes image display 210. Image display may 210 display output from imaging device 110 such as sonogram images. Imaging system 200 also includes augmented display 220. Augmented display 220 may be a touch screen and allow input from the user. Augmented display 220 may overlay tracking information on top of output from imaging device 110. Tracking information may include current tracking status, current location, and/or current insertion depth of the tool being inserted by the user. Overlaid information may also include tool tip location, tool tip distance to a selected target, and feedback information to help guide imaging device 110 and/or the insertion tool. Augmented display 220 may also provide visual feedback (e.g., arrows or animation) to direct the operator to reposition imaging device 110 and/or another medical tool. Augmented display 220 may include one or more speakers to provide audio feedback to the operator to assist in device and tool guidance.

In one embodiment, imaging system 200 may include, for example, an ultrasound probe (e.g., imaging device 110) and one or more displays (e.g., 210 and 220). A first display (e.g., 210) may be configured to communicate with the ultrasound probe to receive ultrasound signals and display images from the ultrasound probe. Imaging component 100 may be at least one of attached to or integral with the ultrasound probe and the imaging device may be configured to communicate with a second display (e.g., 220) to display images from the imaging component 100 and, in some embodiments, images from the ultrasound probe. The first and second display may be the same display. Similarly, the processing units that provide the data to be displayed on the one or more displays may be separate (two or more units) or integrated (one unit). The imaging component 100 may include stabilization assembly 170 (or other stabilization assembly), an imaging device assembly (e.g., 180 and 130) physically coupled to the stabilization assembly, a plurality of light-sensitive devices (e.g., 150) physically coupled to the stabilization assembly, and a memory unit (e.g., 710) physically coupled to the imaging device assembly (e.g., head shell). The memory unit may be configured to store calibration information and/or usage information for the image-guided ultrasound system.

Imaging system 200 may also include a control unit in communication with the feedback device. The control unit may be part of or coupled with the feedback device or the control unit may be separate from the feedback device. In one embodiment an operator 250 may select a target on, for example, display 220. The control unit may receive the target selection. The control unit may also determine the position and pose of the feedback device, imaging device (e.g., ultrasound probe 110) and/or medical tools based on sensors connected to or outside the feedback device, the imaging device (e.g., ultrasound probe 110), and/or medical tools. The control unit may calculate the position and pose of the feedback device, imaging device (e.g., ultrasound probe 110) and/or medical tools to the target location. The control unit may determine if the feedback device, imaging device (e.g., ultrasound probe 110) and/or medical tools, for example, has moved away from the target position or is not or not quickly enough moving towards the target. The control unit may then calculate a deviation to another position and pose of the feedback device (e.g., a position and pose closer to the target or for a better view of the target), imaging device (e.g., ultrasound probe 110) and/or medical tools. The control unit may translate the deviation into control data and transmit the control data to the feedback device. The feedback device can then instruct the operator to guide the feedback device, imaging device (e.g., ultrasound probe 110) and/or medical tools into the new position.

Imaging system 200 may include an image processing module including one or more integrated circuits and/or microprocessors. The image processing module may be located on printed circuit board 140 (or another circuit in the image processing module) and/or may be located externally to imaging component 100 (e.g., an external computer or processing module).

Figure 3:
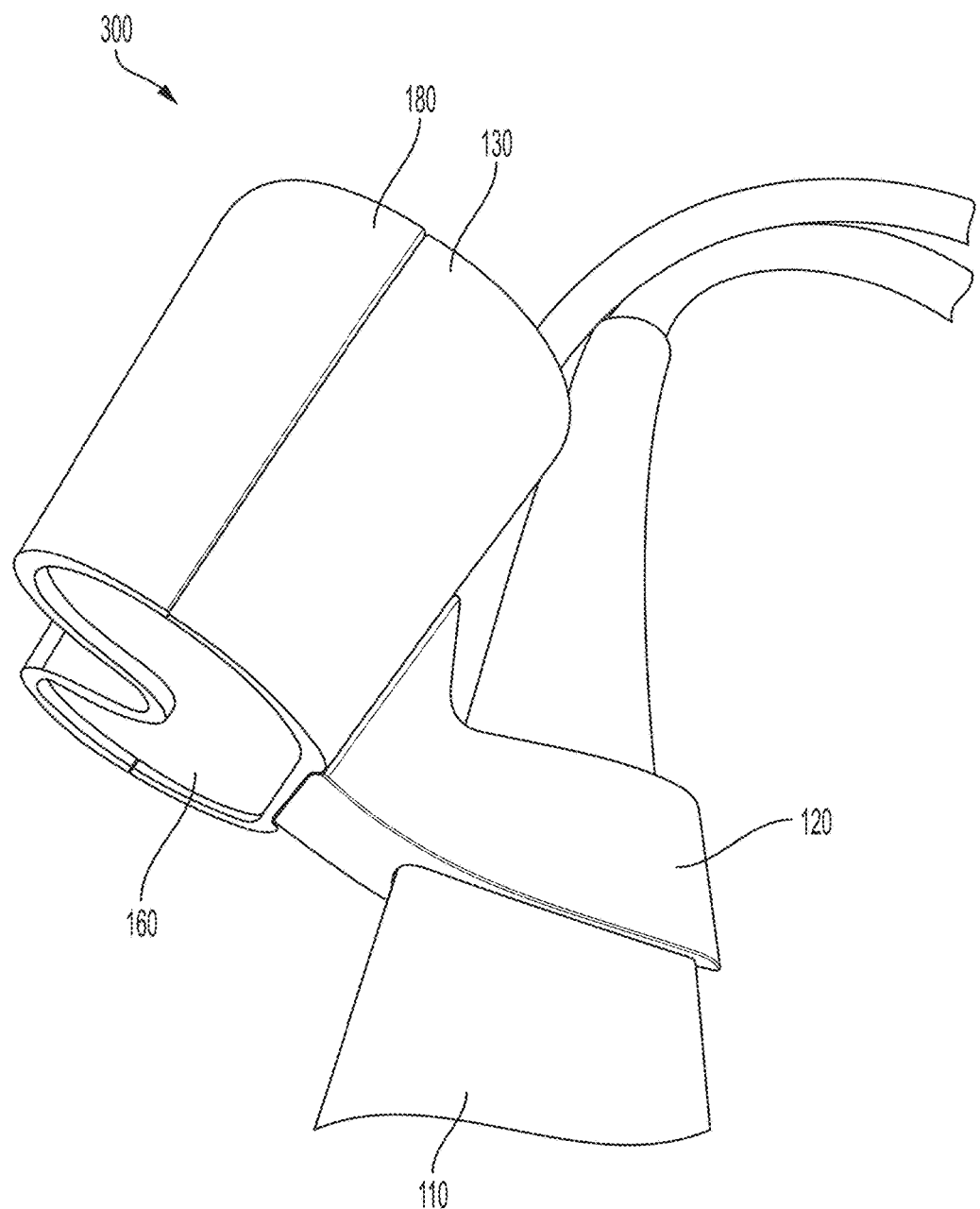
FIG. 3 shows an example imaging component for an example imaging system.

FIG. 3 shows another embodiment of an imaging component for an imaging system according to an embodiment of the current invention. In particular, FIG. 3 shows bracket 120 connected to imaging device 110. Bracket 120 is also connected to bottom shell 130. Bottom shell 130 is connected to top shell 180. Lens 160 may be secured in place between bottom shell 130 and top shell 180. Bottom shell 130 and top shell 180 may house feedback device 300.

Figure 4:
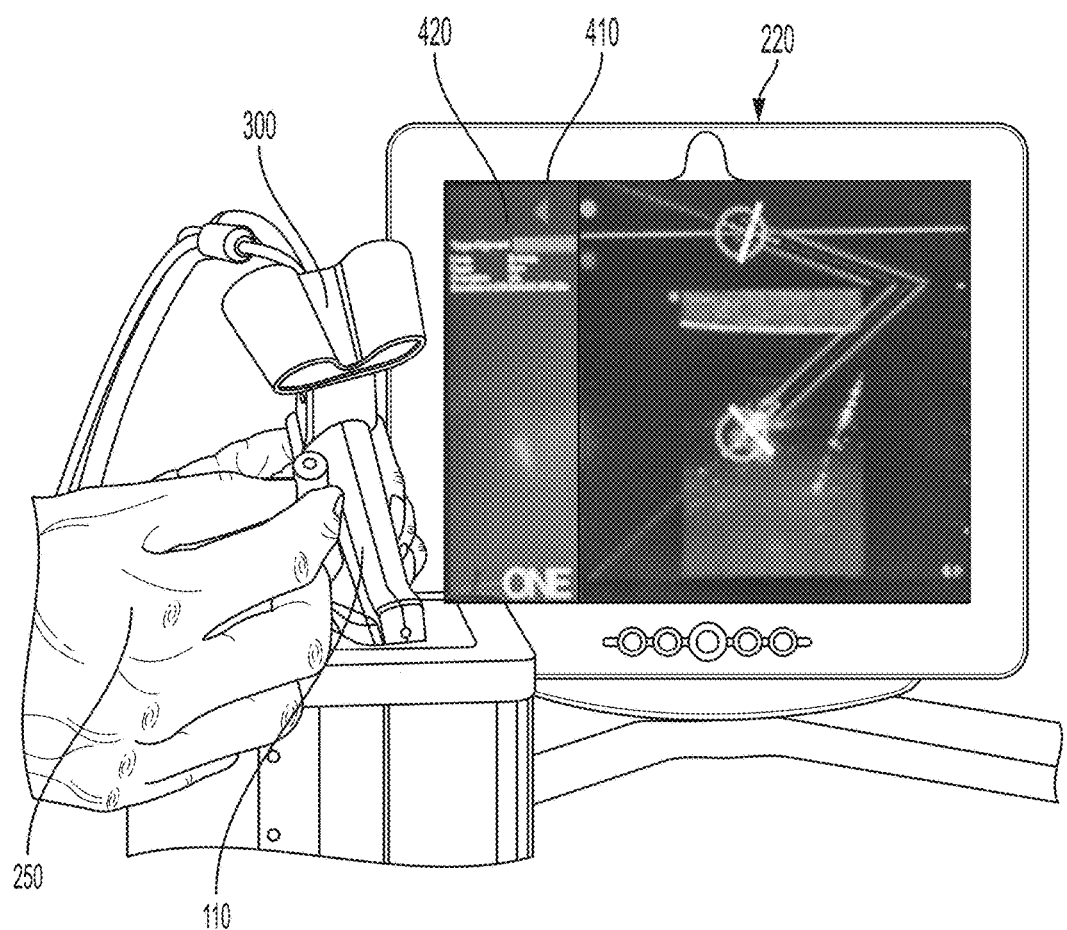
FIG. 4 shows an example feedback device coupled to an imaging device.
Figure 5:
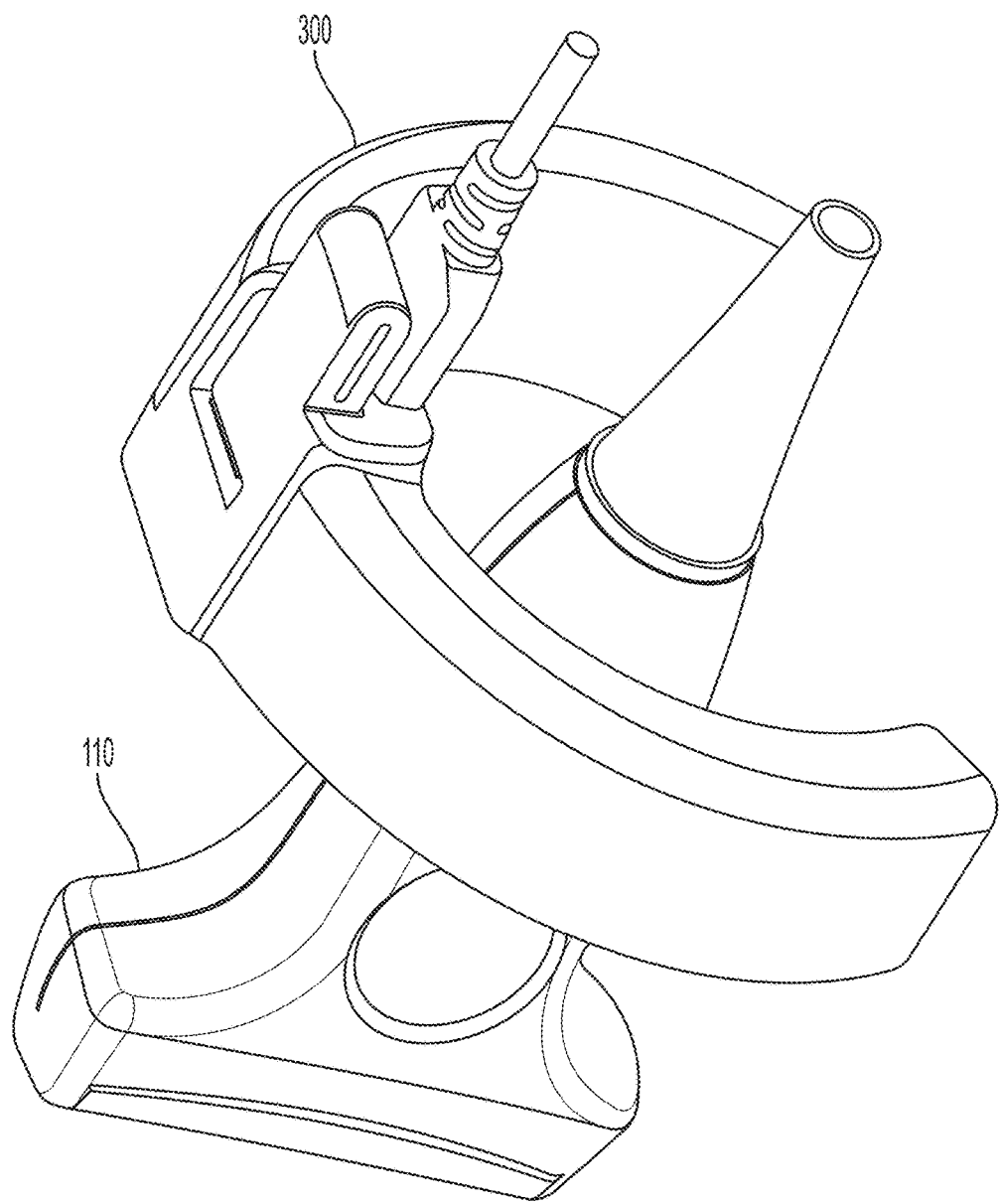
FIG. 5 shows another example feedback device coupled to an imaging device.

FIG. 4 shows an embodiment of a feedback device according to an embodiment of the current invention. FIG. 4 depicts a handheld imaging device 110 (e.g., an ultrasound probe) carries a representative feedback device 300, containing haptic feedback components and sensing components. The imaging device 110 and the feedback device 300 are set up to communicate with a control unit, which computes feedback signals based on at least one of current feedback device pose, instrument pose, imaging device pose, pre-defined target location relative to imaging device, and/or pre-defined target location relative to instrument pose. These feedback signals are then communicated to the operator 250 via audio feedback, visual feedback, and/or haptic feedback device. The configuration of FIG. 4 provides audio feedback (as indicated by sound icon 410 in display 220) and visual feedback via alignment indicator 420 (bar on top-left of display 220) based on, for example, the deviation between target location and instrument pose FIG. 5 depicts another example of feedback device 300 and imaging device 110. In FIG. 5, feedback device wraps partially around and is removably coupled to imaging device 110.

Figure 6:
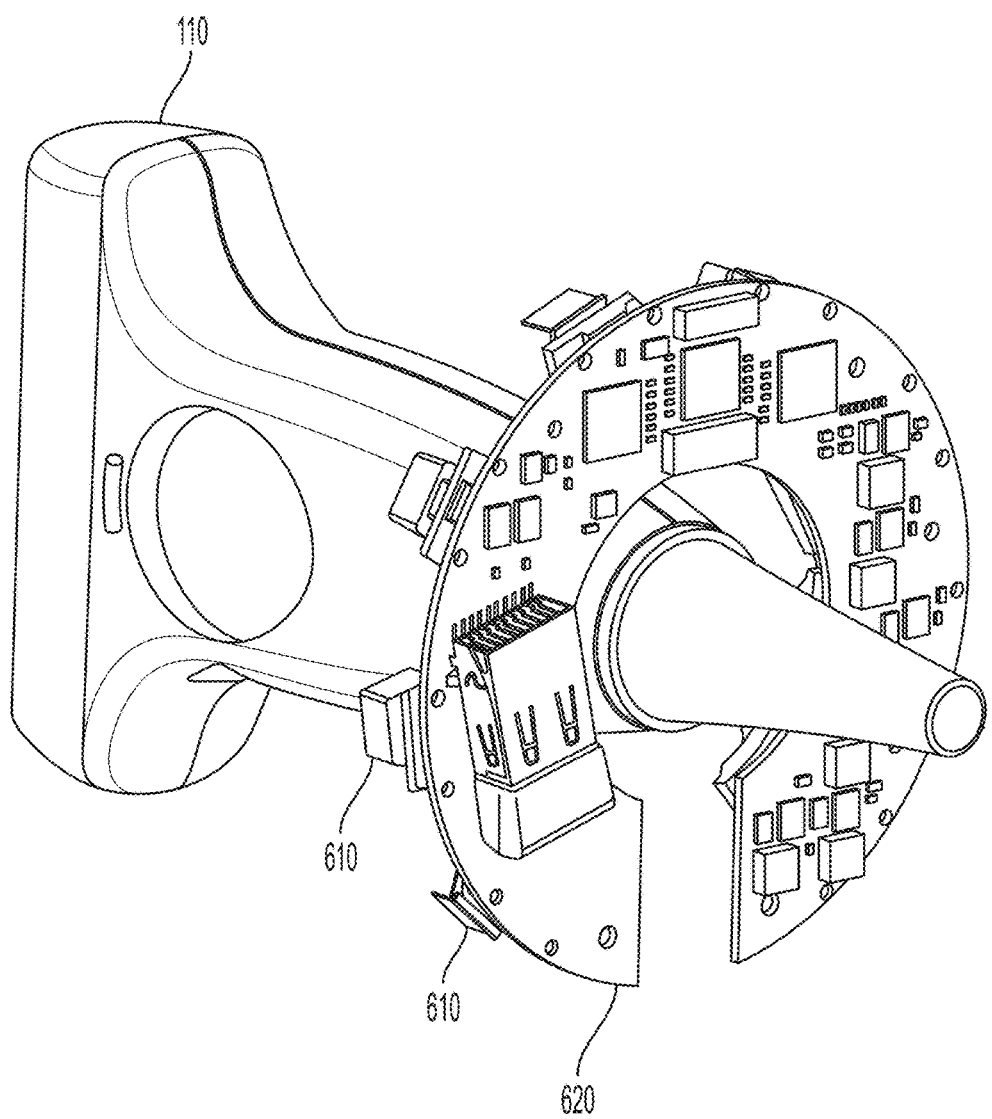
FIG. 6 shows example components of a feedback device.

FIG. 6 shows an example embodiment of components for feedback device 300. FIG. 6 illustrates one embodiment for various components of feedback device 300. Feedback device 300 may include actuators 610 which may be arranged with respective supporting electronics components on a carrier unit 620 close to or around imaging device 110. The specific spatial configuration of the actuators 610 may be dictated by requirements on the degrees of freedom of actuation, i.e. with directions of actuation aligned such that they are non-collinear with multiple degrees of freedom. One example technique to achieve directions of actuation aligned such that they are non-collinear would be to arrange the motor axes of up to three, for example, torque actuators perpendicular to each other, with each axis defining a degree of freedom for torque actuation. The same principle may be independently applied to vibrotactile actuators.

Figure 7:
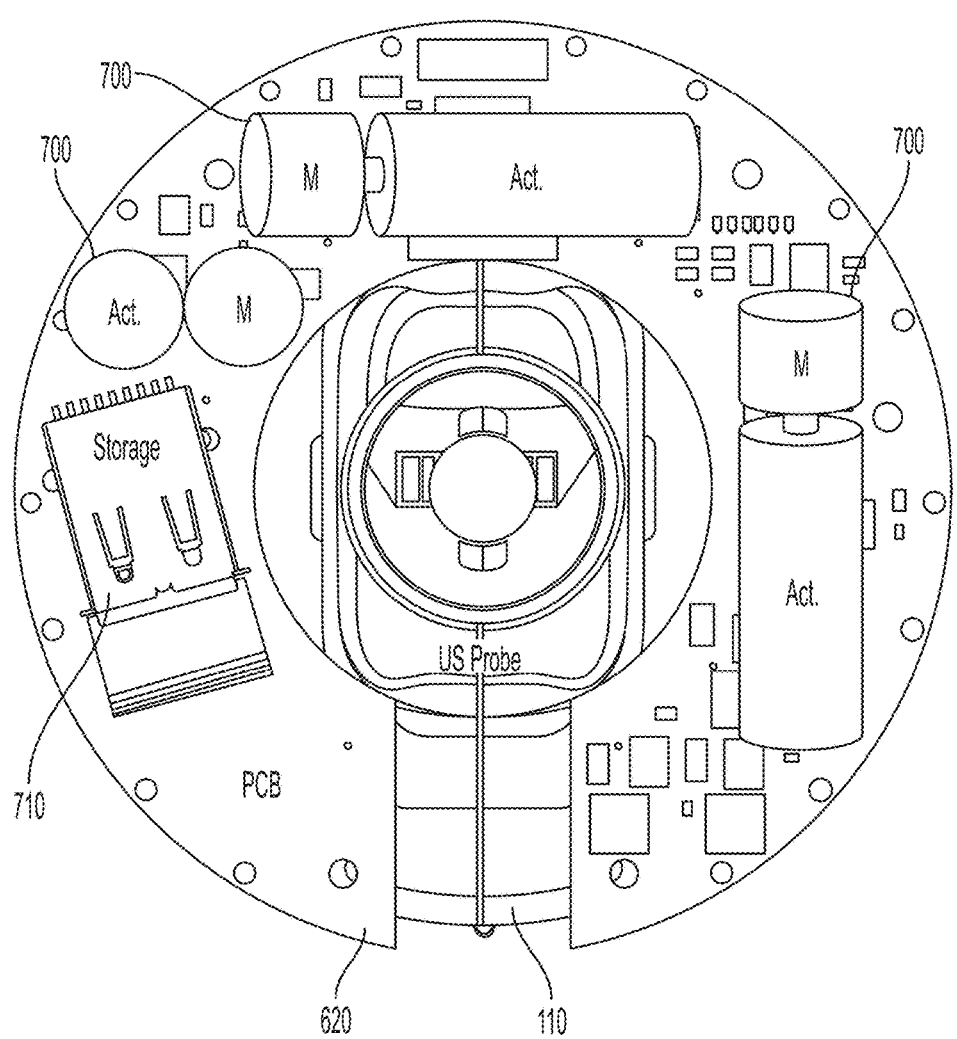
FIG. 7 shows example torque actuator components on a feedback device.

FIG. 7 shows example torque actuator components on an example feedback device 300. Torque actuators 700 (shown as cylinders labeled "Act," with actuated masses "M") are arranged with their respective supporting electronics components on a carrier unit 620 close to or around imaging device 110. The specific spatial configuration of torque actuators 700 may be dictated by requirements on the degrees of freedom of actuation, i.e. with directions of actuation aligned such that they are non-collinear where multiple degrees of freedom are needed. One possible way to achieve this would be to arrange the motor axes of up to three torque actuators 700 perpendicular to each other, with each axis defining a degree of freedom for torque actuation. Carrier unit 620 may also include memory unit 710. Memory unit 710 may be configured to store calibration information and/or usage information.

Figure 8:
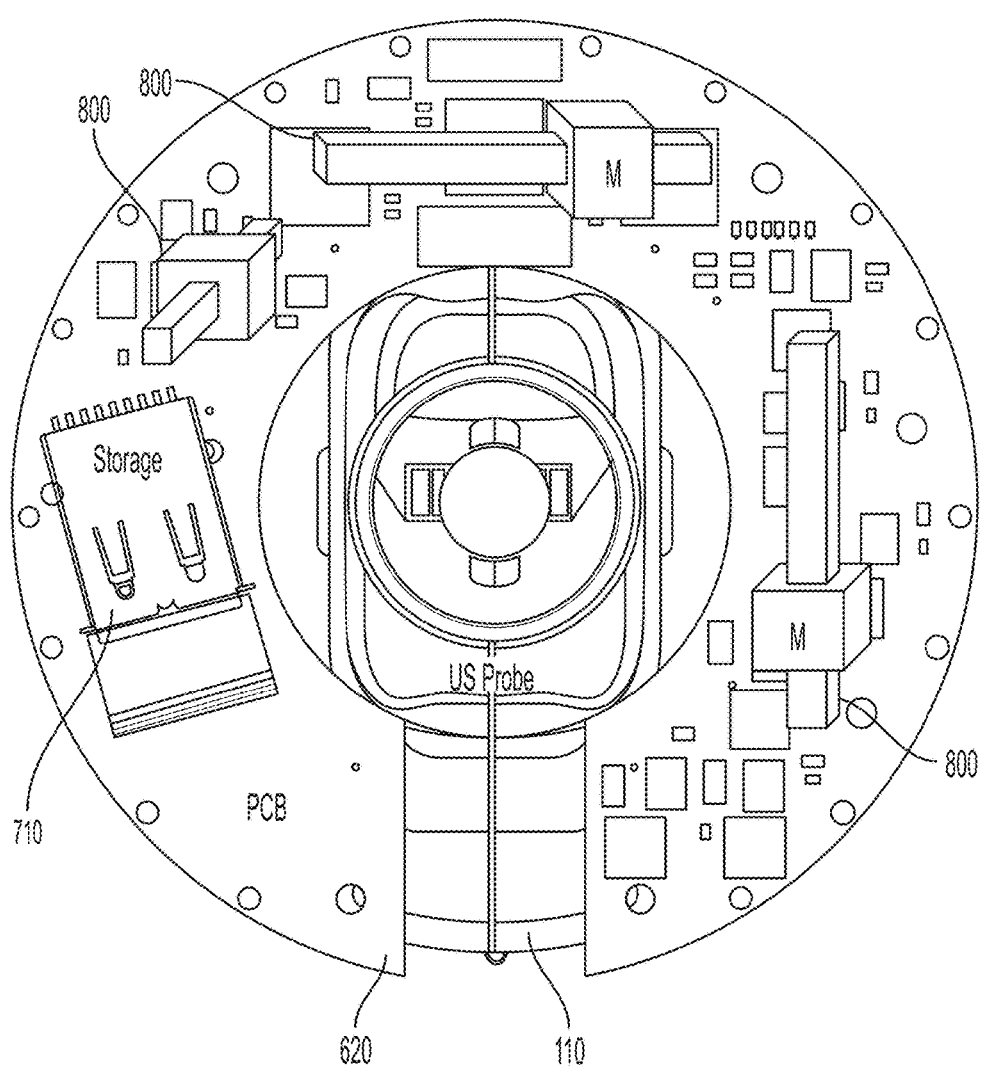
FIG. 8 shows example vibrotactile components on a feedback device.

FIG. 8 shows example vibrotactile components on an example feedback device 300. Vibrotactile actuators 800

(shown as cylinders labeled "Act," with actuated masses "M") are arranged with their respective supporting electronics components on a carrier unit 620 close to or around imaging device 110. The specific spatial configuration of vibrotactile actuators 800 may be dictated by requirements on the degrees of freedom of actuation, i.e. with directions of actuation aligned such that they are non-collinear where multiple degrees of freedom are needed. One possible way to achieve this would be to arrange the motor axes of up to three vibrotactile actuators 800 perpendicular to each other, with each axis defining a degree of freedom for vibrotactile actuation.

Figure 9:
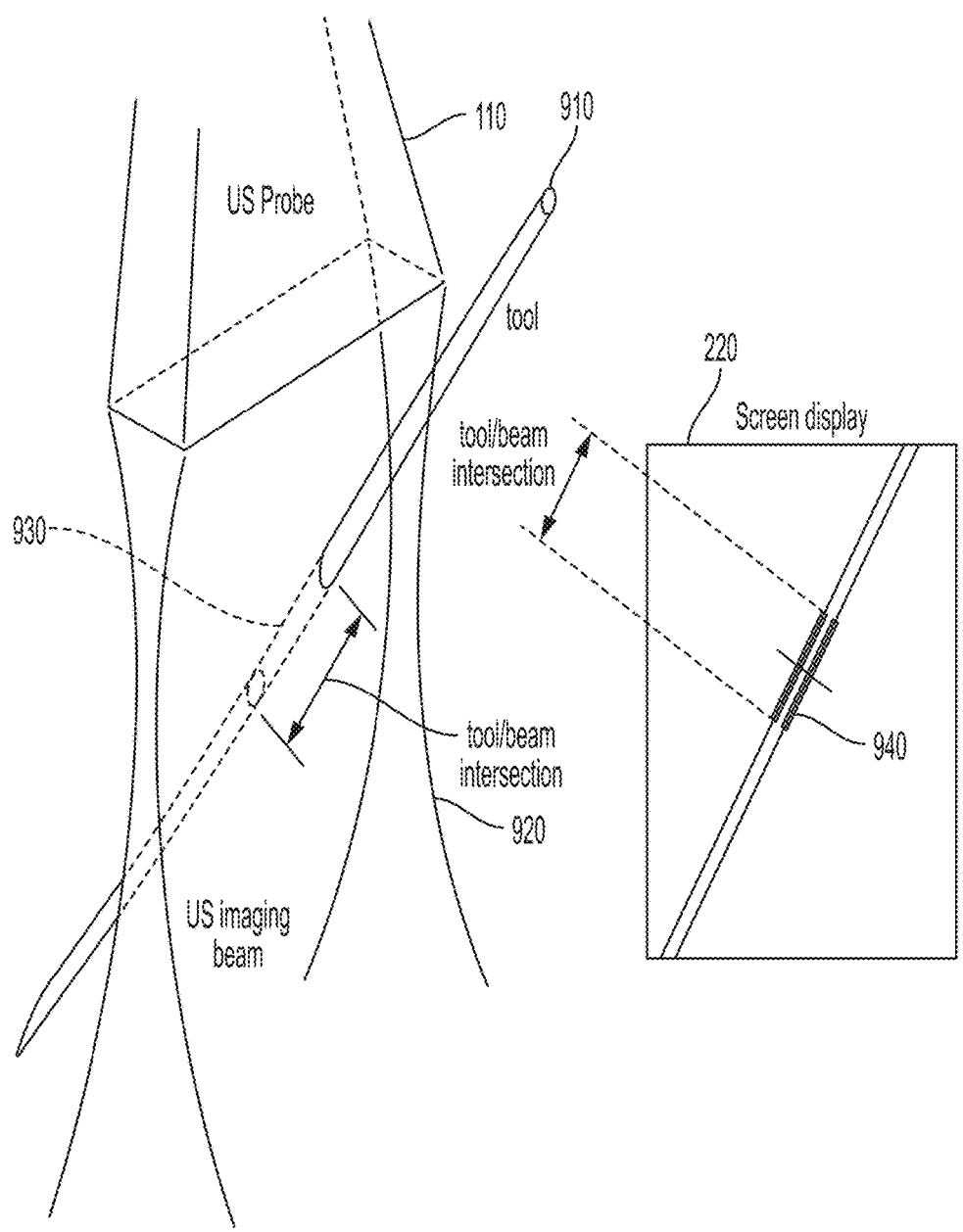
FIG. 9 illustrates an example intersection of a tool and an ultrasound beam.

FIG. 9 illustrates the intersection of a tool 910 and ultrasound beam 920 from imaging device 110 as an ultrasound probe. The image processing module may execute instructions for tracking a medical tool 910 (e.g., a needle, a pointer, a biopsy tool, a laparoscope, an ablation device, a surgical instrument, or an elongated tool). Image processing module may first register the tool with the imaging device, where the position of the tool 910 is known with respect to the imaging device. A representation of tool 910 may be presented on display 220. The processing module may receive a selection of a target (e.g., a tumor, a vessel, a suspicious lesion, or other clinically relevant sites) in the images from the ultrasound probe, or may receive the target selection based on other imaging data introduced into the system (such as pre-defined target sites in CT or MRI data, later to be registered to the imaging device). The selection may be received from a touchscreen displaying the ultrasound images, for example. The module may also track tool 910, display a representation of tool 910 in the display as tool 910 is being tracked. The module may indicate a tool tip in the display (e.g., though the use of one or more perpendicular lines, pointed line arrangements, and/or color variations). Additionally, the module may calculate a distance between the tool tip and the target. A speaker may output audio, wherein the audio changes based on the calculated distance between the tool tip and the target. Display 220 may show the calculated distance between the tool tip and the target; output visual cues as to the quality of the tool tracking; and/or indicate a loss of tool tracking though audio, visual, and/or haptic cues. The processing module may further display the tracked tool 910 as a line and may represent the quality of the tool tracking as a function of a length of the displayed line. In a specific example of a tracked tool 910 intersecting the ultrasound imaging area at 930, there may be a certain segment of the tool 910 physically contained within the volume of the ultrasound beam 920. The length of this segment can be computed by the processing module based on knowledge about the standard beam shape, and may be displayed as overlaid variations in color or length or as overlaid markers 940 on the displayed tool representation itself.

Figure 10:
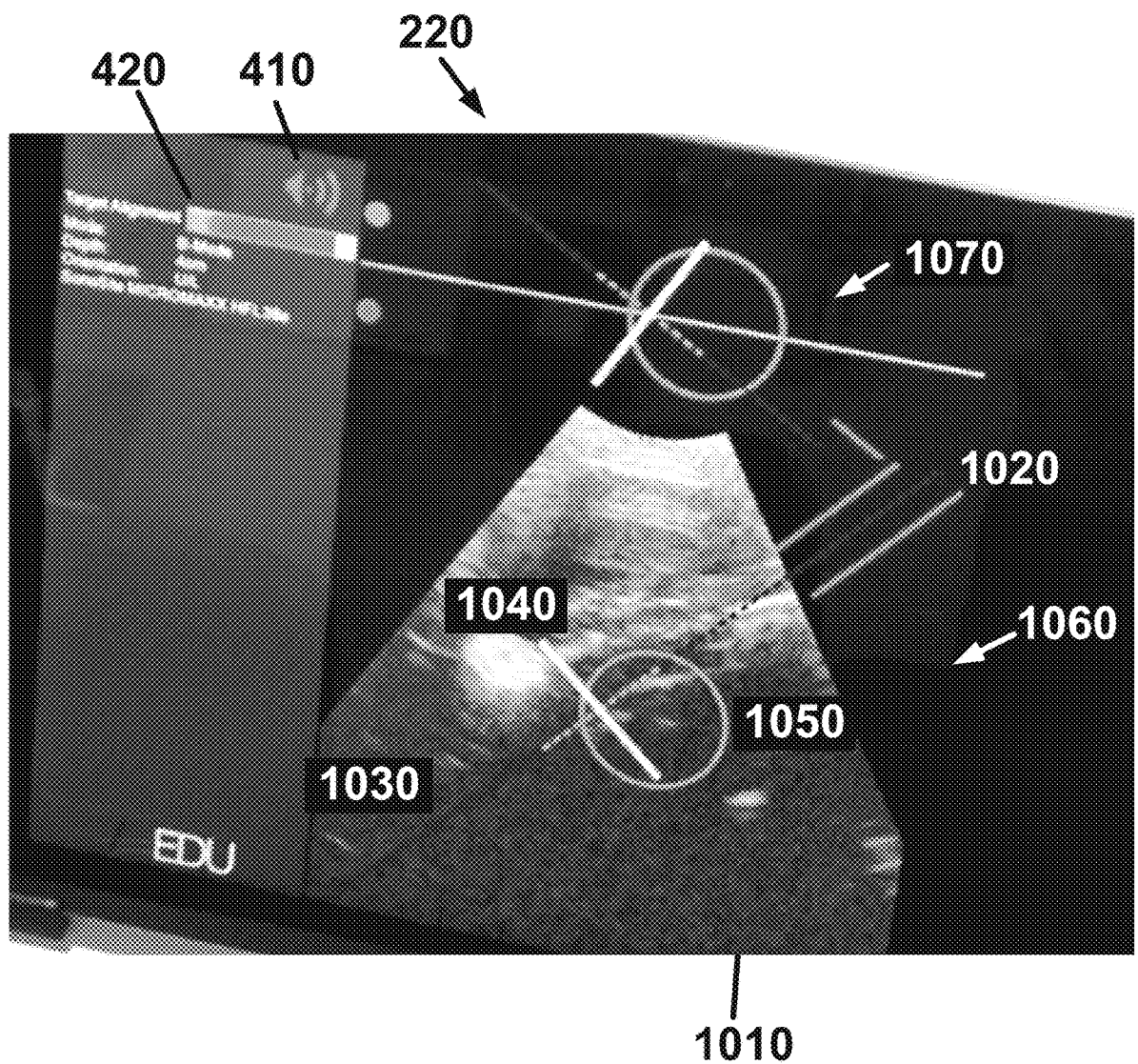
FIG. 10 shows an example screenshot of a tool-tip display.

FIG. 10 shows an example screenshot of a tool-tip display in an embodiment according to an embodiment of the current invention. FIG. 10 includes a screen shot from display 220 including live ultrasound image 1010. Display 220 also shows a representation of the medical tool 1020 indicating tool's 910 current position (indicated by double magenta lines), the tip indicated by the end of the double magenta lines. A dotted blue/green line indicates the future trajectory 1030 of medical tool 910. A perpendicular yellow line 1040 may indicate the intersection of tool trajectory and ultrasound image plane. Target 1050 (a green circle) may indicate an operator selected target location. Target alignment indicator 420 (a green status bar) may indicate the absolute deviation between tool trajectory and target location and may be used for guidance towards target 1050. Sound icon 410 may indicate audio feedback. The depicted navigation-related representations show a projection onto the 2D live ultrasound image 1060 as well as a projection onto a top-down/bird's-eye view of the imaging device environment 1070.

Although FIGS. 1-10 illustrate the imaging system as an ultrasound imaging system and that the bracket 120 is structured to be attached to an imaging device 110 as an ultrasound probe, the broad concepts of the current invention are not limited to this example. The bracket may be structured to be attachable to other imaging systems, such as, but not limited to, x-ray and magnetic resonance imaging systems, for example.

Figure 11:
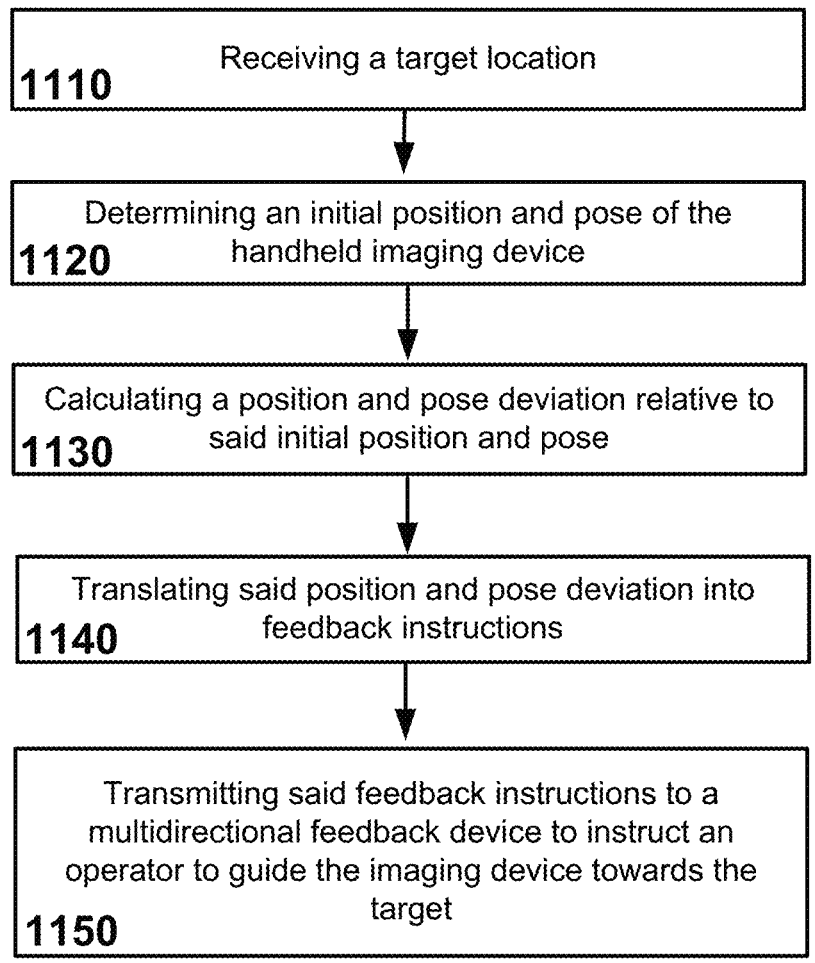
FIG. 11 depicts an example workflow.

FIG. 11 depicts an example workflow according to an embodiment of the current invention. In 1110, a selection of target 1050 may be received. Target 1050 may be selected by operator 250 selecting a region of interest via, for example, augmented display 220. Target information (e.g., location relative to the imaging device 110, or approximately relative to patient anatomy in case of probe tracking allowing updates to the initial operator-selected target location 1050) may be transmitted to the control unit. From 1110, flow may move to 1120.

In 1120, the control unit may determine an initial position and pose of the imaging device 110 (e.g., ultrasound probe) and/or feedback device. The position and pose may include the location and rotation of imaging device 110. From 1120, flow may move to 1130.

In 1130, the control unit may calculate a position and pose deviation relative to the initial position and pose. The deviation calculation may be with respect to an imaging device 110 that is moving away from targeted area 1050 or not moving towards targeted area 1050 quickly enough. In one embodiment, the control unit may calculate another position for the imaging device 110. From 1130, flow may move to 1140.

In 1140, the control unit may translate the position and pose deviation into feedback instructions. The feedback instructions providing instructions on moving the imaging device 110 towards target 1050 or towards a new position for the imaging device. In one embodiment, the control unit may constantly calculate and recalculate relative pose. For example, sensors may provide a relative pose between the multidirectional feedback device and the handheld imaging device (if separate) and the control unit may calculate a new pose deviation based on the pose deviation of the imaging device and the relative pose between the multidirectional feedback device and the imaging device. From 1140, flow may move to 1150.

In 1150, the control unit may transmit the control instructions to multidirectional feedback device 300. Feedback device 300 may use the received instructions to instruct an operator to guide the imaging device 110 towards target 1050 or towards the new position for the imaging device 110. The guidance being one of directional haptic feedback, audio feedback, and/or video feedback. In one embodiment, the multidirectional feedback device 300 may provide operator 250 with feedback to continuously position the handheld imaging device 110 or a medical tool 910 within safe operation pose boundaries that are predefined, updated during system operation, or a combination of predefined and updated during system operation. From 1150, flow may end.

In an embodiment, tracking of a medical tool 910 (e.g., needle, surgical instrument) may be accomplished through one or more visible features on tool 910. (Basic tool tracking has been described in previous publications by the inventors, such as Stolka et al. "Navigation with local sensors in handheld 3D ultrasound: initial in-vivo experience," SPIE Medical Imaging 2011, Lake Buena Vista, Fla./USA, pp. 79681J-79681J. International Society for Optics and Photonics, 2011, and Wang et al. "The Kinect as an interventional tracking system," SPIE Medical Imaging, San Diego, Calif., USA, pp. 83160U-83160U. International Society for Optics and Photonics, 2012, both of which are included by reference in their entirety.) The visible feature may include a detectable pattern, the pattern being initially created using a pseudo random binary sequence, or more generally a de Bruijn sequence, wherein the pattern is one of marked, printed, etched, or applied to tool 910. The pattern may be used to detect insertion depth of tool 910 into a human or animal body. Alternatively, the visible feature may include an attachment such as a ring attached to the tool. The ring may be reflective and/or cylindrical or handle shaped. The ring may include a detectable pattern used in calculating an insertion depth of the tip of the tool, the detectable pattern may be initially created using a pseudo random binary sequence. Imaging system 200 may initially calculate a distance from the ring to the tip of the tool and use this calculated distance to calibrate the imaging system 200 for tool tracking.

The displayed information to assist in medical tool 910 positioning may include information about the length of intersection between the medical tool 910 and the non-infinitesimally thin ultrasound imaging plane, by drawing markers on the medical tool line to denote the extent of said intersection. In other words, a line may indicate the medical tool trajectory, wherein a portion of the line may be shaded differently to indicate the area where the medical tool 910 will cross the imaging plane of the ultrasound.

Insertion depth calculation may be made based on the one or more visible features on tool 910. Because of the nature of the visible feature, the insertion depth of the tip of tool 910 may be correctly calculated even when a portion of the one or more visible features is not viewable by the one or more light sensitive devices. For example, when the visible feature includes the detectable pattern created using a pseudo random binary sequence, the pattern is non-periodic and unique over small segments. Therefore, even if a small portion of the pattern is visible, imaging system 200 may still calculate the insertion depth. Tool tip location may be calculated (e.g., candidate tip locations) using the one or more visible features. The calculated tip locations may be in a three dimensional plane and may be based on the insertion location, calculated insertion depth, and angle of entry of the medical tool. Insertion depth of the tool tip and possible tip locations may be displayed on augmented display 220. A surgeon or other medical personal may use the displayed information when performing an IGI, for example.

The following describes one possible technique of localizing the medical tool tip in stereo images using the pattern on the medical tool shaft in an embodiment. Given a pair of stereo images (left and right light-sensitive device images) and light-sensitive device calibration (intrinsic and extrinsic light-sensitive device parameters), the first step of tip localization is to rectify the left and right images. Next, the medical tool is detected in these images as straight lines centered at the middle of the shaft. In order to localize the tip of the medical tool in 3D, the medical tool line is reconstructed in 3D space. This line is then sampled with a constant delta providing a set of 3D points. These points are then projected back into the left and right images resulting in two sets of 2D points for the left and right rectified images. Then, the pixel intensities at these points are computed using interpolation. This will generate two intensity vectors with regular sampling. In the next step, the two intensity vectors are correlated against all possible "sub-patterns." A sub-pattern is a minimal continuous portion of the whole pattern that could be uniquely identified. For each sub-pattern, the location that maximizes correlation and the correlation value is recorded. The sub-patterns with the highest correlation value is selected in the left and right vectors. Since the offset of the sub-pattern with respect to the tip is known, the 3D location of the tip can be estimated. Note that left and right images provide two almost independent estimates of the tip location. As a verification step, the two estimated tip locations should be closer than a threshold. The final tip location is given as the weighted-average of these two estimated tip positions.

In another embodiment, light waves may be filtered by the one or more light sensitive devices to only allow light of a specific wavelength and to restrict light of other wavelengths. A coating may be applied to the medical tool or other tool that may be illuminated based on receiving light of a specific wavelength. The coating may produce or reflect a light of the specific wavelength. The reflected or produced light of a specific wavelength may be detected by the light sensitive devices. The reflected or produced light of a specific wavelength may reduce the occurrence of false positives. Further, the coating may only illuminate or produce light of a specific wavelength to reveal the detectable pattern. The possible tip locations and insertion depth of the tip of the medical tool or tool may be calculated based on based on the displayed detectable pattern of light in a specific wavelength.

Illustrative Computer System

Figure 12:
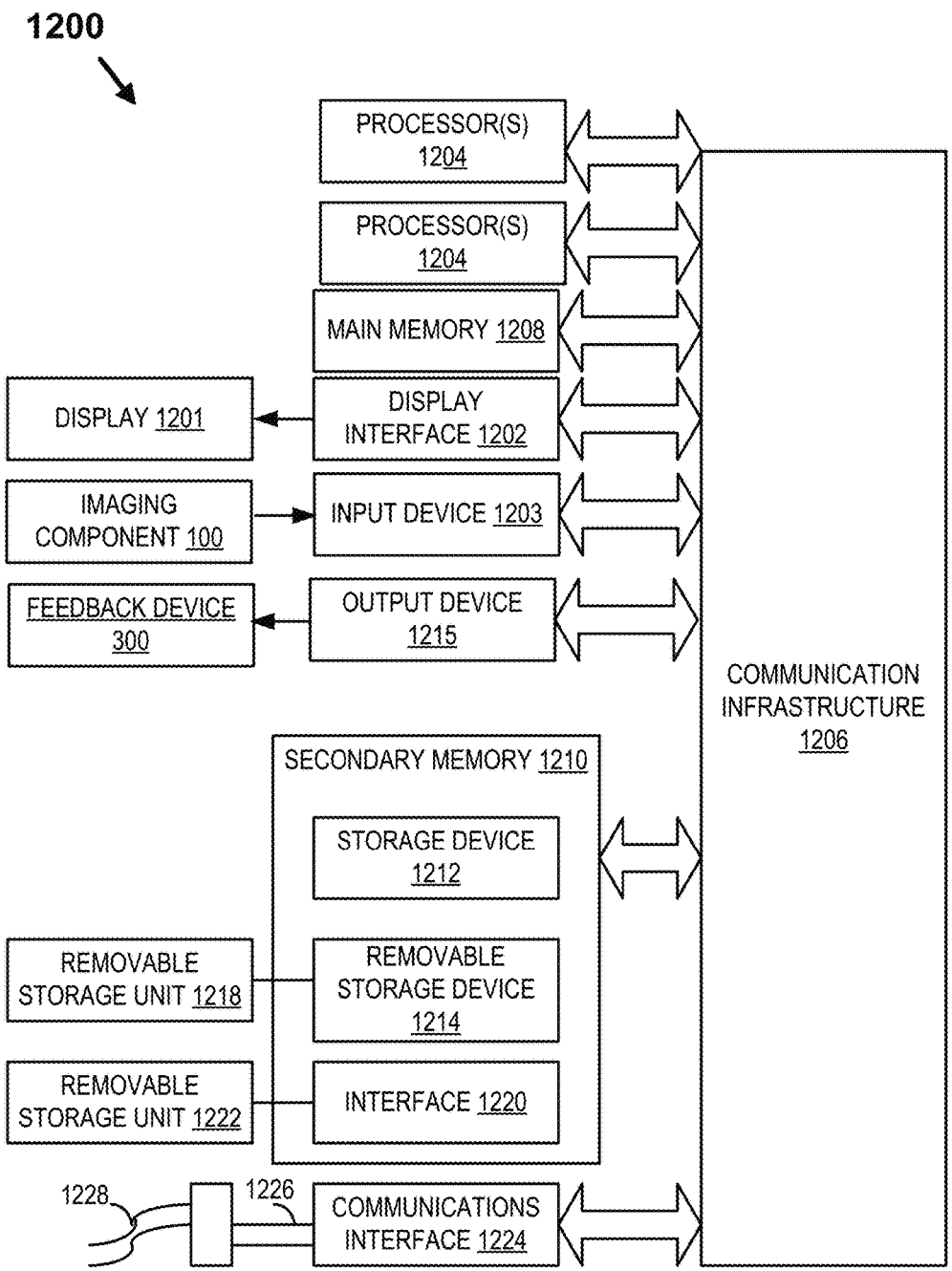
FIG. 12 depicts an illustrative embodiment of a computer for performing the methods and building the devices and systems described herein.

FIG. 12 depicts an illustrative computer system that may be used in implementing an illustrative embodiment of the present invention. Specifically, FIG. 12 depicts an illustrative embodiment of a computer system 1200 that may be used in computing devices such as, e.g., but not limited to, standalone or client or server devices. FIG. 12 depicts an illustrative embodiment of a computer system that may be used as client device, or a server device, etc. The present invention (or any part(s) or function(s) thereof) may be implemented using hardware, software, firmware, or a combination thereof and may be implemented in one or more computer systems or other processing systems. In fact, in one illustrative embodiment, the invention may be directed toward one or more computer systems capable of carrying out the functionality described herein. An example of a computer system 1200 is shown in FIG. 12, depicting an illustrative embodiment of a block diagram of an illustrative computer system useful for implementing the present invention. Specifically, FIG. 12 illustrates an example computer 1200, which in an illustrative embodiment may be, e.g., (but not limited to) a personal computer (PC) system running an operating system such as, e.g., (but not limited to) MICROSOFT® WINDOWS® NT/98/2000/XP/Vista/Windows 7/Windows 8, etc. available from MICROSOFT® Corporation of Redmond, Wash., U.S.A. or an Apple computer or tablet executing MAC® OS, OS X, or iOS from Apple® of Cupertino, Calif., U.S.A., or a computer running a Linux or other UNIX derivative. However, the invention is not limited to these platforms. Instead, the invention may be implemented on any appropriate computer system running any appropriate operating system. In one illustrative embodiment, the present invention may be implemented on a computer system operating as discussed herein. An illustrative computer system, computer 1200 is shown in FIG. 12. Other components of the invention, such as, e.g., (but not limited to) a computing device, a communications device, a telephone, a personal digital assistant (PDA), an iPhone, an iPad, a Surface, and Android device, a 3G/4G wireless device, an LTE device, a wireless device, a personal computer (PC), a handheld PC, a laptop computer, a smart phone, a mobile device, a netbook, a handheld device, a portable device, an interactive television device (iTV), a digital video recorder (DVR), client workstations, thin clients, thick clients, fat clients, proxy servers, network communication servers, remote access devices, client computers, server computers, peer-to-peer devices, routers, web servers, data, media, audio, video, telephony or streaming technology servers, etc., may also be implemented using a computer such as that shown in FIG. 12. In an illustrative embodiment, services may be provided on demand using, e.g., an interactive television device (iTV), a video on demand system (VOD), via a digital video recorder (DVR), and/or other on demand viewing system. Computer system 1200 and/or parts of computer system 1200 may be used to implement the network, processing device, and/or components as described in FIGS. 1-11. Such as imaging component 100, printed circuit board 140, other devices of imaging system 200, the control unit, feedback device 300, and/or components of the feedback device (e.g., haptic actuators).

The computer system 1200 may include one or more processors, such as, e.g., but not limited to, processor(s) 1204. The processor(s) 1204 may be connected to a communication infrastructure 1206 (e.g., but not limited to, a communications bus, cross-over bar, interconnect, or network, etc.). Processor 1204 may include any type of processor, microprocessor, or processing logic that may interpret and execute instructions (e.g., for example, a field programmable gate array (FPGA)). Processor 1204 may comprise a single device (e.g., for example, a single core) and/or a group of devices (e.g., multi-core). The processor 1204 may include logic configured to execute computer-executable instructions configured to implement one or more embodiments. The instructions may reside in main memory 1208 or secondary memory 1210. Processors 1204 may also include multiple independent cores, such as a dual-core processor or a multi-core processor. Processors 1204 may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

Computer system 1200 may include a display interface 1202 that may forward, e.g., but not limited to, graphics, text, and other data, etc., from the communication infrastructure 1206 (or from a frame buffer, etc., not shown) for display on the display unit 1201. The display unit 1201 may be, for example, a television, a computer monitor, iPad, a mobile phone screen, display 210, display 220, etc. The output may also be provided as sound through, for example, a speaker.

The computer system 1200 may also include, e.g., but is not limited to, a main memory 1208, random access memory (RAM), and a secondary memory 1210, etc. Main memory 1208, random access memory (RAM), and a secondary memory 1210, etc., may be a computer-readable medium that may be configured to store instructions configured to implement one or more embodiments and may comprise a random-access memory (RAM) that may include RAM devices, such as Dynamic RAM (DRAM) devices, flash memory devices, Static RAM (SRAM) devices, etc.

The secondary memory 1210 may include, for example, (but is not limited to) a hard disk drive 1212 and/or a removable storage drive 1214, representing a floppy diskette drive, a magnetic tape drive, an optical disk drive, a compact disk drive CD-ROM, flash memory, etc. The removable storage drive 1214 may, e.g., but is not limited to, read from and/or write to a removable storage unit 1218 in a well-known manner. Removable storage unit 1218, also called a program storage device or a computer program product, may represent, e.g., but is not limited to, a floppy disk, magnetic tape, optical disk, compact disk, etc. which may be read from and written to removable storage drive 1214. As will be appreciated, the removable storage unit 1218 may include a computer usable storage medium having stored therein computer software and/or data. Secondary memory 1210 may also include memory unit 710.

In alternative illustrative embodiments, secondary memory 1210 may include other similar devices for allowing computer programs or other instructions to be loaded into computer system 1200. Such devices may include, for example, a removable storage unit 1222 and an interface 1220. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units 1222 and interfaces 1220, which may allow software and data to be transferred from the removable storage unit 1222 to computer system 1200.

Computer 1200 may also include an input device 1203 which may include any mechanism or combination of mechanisms that may permit information to be input into computer system 1200 from, e.g., a user. Input device 1203 may include logic configured to receive information for computer system 1200 from, e.g. a user. Examples of input device 1203 may include, e.g., but not limited to, a mouse, pen-based pointing device, or other pointing device such as a digitizer, a touch sensitive display device, and/or a keyboard or other data entry device (none of which are labeled). Other input devices 1203 may include, e.g., but not limited to, a biometric input device, a video source, an audio source, a microphone, a web cam, a video camera, a light-sensitive device, and/or other camera. Data and/or images from imaging component 100 (e.g., imaging device 110, light-sensitive devices 150, sensing elements such as accelerometers, gyroscopes, and/or magnetometers).

Computer 1200 may also include output devices 1215 which may include any mechanism or combination of mechanisms that may output information from computer system 1200. Output device 1215 may include logic configured to output information from computer system 1200. Embodiments of output device 1215 may include, e.g., but not limited to, display 1201, and display interface 1202, including displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc. Computer 1200 may include input/output (I/O) devices such as, e.g., (but not limited to) input device 1203, communications interface 1224, cable 1228 and communications path 1226, etc. These devices may include, e.g., but are not limited to, a network interface card, and/or modems. Output device may also include feedback device 300 and feedback components (e.g., vibrotactile feedback actuators 800, torque feedback actuators 700, displays 210, 220, LEDs, speakers, etc.).

Communications interface 1224 may allow software and data to be transferred between computer system 1200 and external devices.

In this document, the terms "computer program medium" and "computer readable medium" may be used to generally refer to media such as, e.g., but not limited to, removable storage drive 1214, a hard disk installed in hard disk drive 1212, memory unit 710, flash memories, removable discs, non-removable discs, etc. In addition, it should be noted that various electromagnetic radiation, such as wireless communication, electrical communication carried over an electrically conductive wire (e.g., but not limited to twisted pair, CAT5, etc.) or an optical medium (e.g., but not limited to, optical fiber) and the like may be encoded to carry computer-executable instructions and/or computer data that embodiments of the invention on e.g., a communication network. These computer program products may provide software to computer system 1200. It should be noted that a computer-readable medium that comprises computer-executable instructions for execution in a processor may be configured to store various embodiments of the present invention. References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic.

Further, repeated use of the phrase "in one embodiment," or "in an illustrative embodiment," do not necessarily refer to the same embodiment, although they may. The various embodiments described herein may be combined and/or features of the embodiments may be combined to form new embodiments.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments of the present invention may include apparatuses for performing the operations herein. An apparatus may be specially constructed for the desired purposes, or it may comprise a general purpose device selectively activated or reconfigured by a program stored in the device.

Embodiments may be embodied in many different ways as a software component. For example, it may be a stand-alone software package, or it may be a software package incorporated as a "tool" in a larger software product, such as, for example, a scientific modeling product. It may be downloadable from a network, for example, a website, as a stand-alone product or as an add-in package for installation in an existing software application. It may also be available as a client-server software application, or as a web-enabled software application. It may also be part of a system for detecting network coverage and responsiveness. A general purpose computer may be specialized by storing programming logic that enables one or more processors to perform the techniques indicated herein and the steps of, for example, FIG. 11.

Embodiments of the present invention may include apparatuses for performing the operations herein. An apparatus may be specially constructed for the desired purposes, or it may comprise a general purpose device selectively activated or reconfigured by a program stored in the device.

Embodiments may be embodied in many different ways as a software component. For example, it may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, or as a web-enabled software application.

While various embodiments of the present invention have been described above, it should be understood that they have been presented by way of example only, and not limitation. Thus, the breadth and scope of the present invention should not be limited by any of the above-described illustrative embodiments, but should instead be defined only in accordance with the following claims and their equivalents.

We claim:

1. A system for guided navigation during a medical procedure, the system comprising:
    a handheld imaging device;
    a medical interventional tool having one or more detectable markings, the one or more detectable markings comprising a pattern created using a pseudo random binary sequence or a de Bruijn sequence;
    a multidirectional feedback device configured to detect a pose of the handheld imaging device and provide a feedback to an operator on said pose of the handheld imaging device to assist the operator in positioning the medical intervention tool to or near a target location;
    a control unit in communication with the multidirectional feedback device and the handheld imaging device, the control unit configured to:
        receive the target location,
        determine an initial pose of the handheld imaging device,
        calculate a pose deviation relative to said initial pose of the handheld imaging device,
        translate said pose deviation into control data,
        transmit said control data to the multidirectional feedback device, and
        obtain a trajectory of the medical intervention tool based on the one or more detectable markings provided on the medical intervention tool; and
    wherein said multidirectional feedback device uses said control data to provide the operator with the feedback to guide at least one of the handheld imaging device and the medical intervention tool towards the target, wherein the feedback further indicates deviation between the target location and the trajectory of the medical intervention tool.

2. The system of claim 1, wherein the multidirectional feedback device is at least one of: an ungrounded haptic feedback device, an audio feedback device, or a visual feedback device.

3. The system of claim 1, wherein the multidirectional feedback device comprises at least one of: an accelerometer, a gyroscope, a magnetometer, or optical sensors.

4. The system of claim 1, wherein the multidirectional feedback device is a haptic feedback device and includes one or more actuators comprising one or more: vibrotactile feedback actuators or torque feedback actuators.

5. The system of claim 4, wherein the torque feedback actuators generate torque impulses generated by one or more asymmetrical-impulse-driven flywheels and the vibrotactile feedback actuators generate vibrotactile impulses generated by one or more asymmetric vibration actuators.

6. The system of claim 5, wherein at least one of the one or more asymmetrical-impulse-driven flywheels are oriented so as to be linearly independent or at least one of the one or more asymmetric vibration actuators are oriented so as to be linearly independent.

7. The system of claim 1, wherein the multidirectional feedback device is one of: removably attached to the handheld imaging device, integrated into the handheld imaging device, or separate from the handheld imaging device.

8. The system of claim 1, wherein the handheld imaging device is an ultrasound probe.

9. The system of claim 1, wherein the multidirectional feedback device provides the operator with feedback to continuously position the handheld imaging device along a time-varying path.

10. The system of claim 1, wherein the multidirectional feedback device provides the operator with feedback to continuously position the handheld imaging device within predefined operation pose boundaries, within updated operation pose boundaries that are updated during system operation, or within a combination of predefined operation pose boundaries and updated operation pose boundaries.

11. The system of claim 1, further comprising:
the medical intervention tool for insertion into a patient, wherein the control unit determines a pose of the medical intervention tool and provides the operator with feedback to guide the medical intervention tool to the target.

12. The system of claim 11, wherein the multidirectional feedback device is removably attached to the medical intervention tool.

13. The system of claim 11, wherein the multidirectional feedback device provides the operator with feedback to continuously position the medical intervention tool along a time-varying path.

14. The system of claim 11, wherein the multidirectional feedback device provides the operator with feedback to continuously position the medical intervention tool within predefined operation pose boundaries, within updated operation pose boundaries that are updated during system operation, or within a combination of predefined operation pose boundaries and updated operation pose boundaries.

15. A method of guided navigation during a medical procedure, the method comprising:
receiving by a control unit a target location;
determining by the control unit an initial pose of a handheld imaging device;
calculating by the control unit a pose deviation relative to said initial pose of the handheld imaging device;
translating by the control unit said pose deviation into control data;
obtaining by the control unit a trajectory of a medical intervention tool based on one or more detectable markings provided on the medical intervention tool, the one or more detectable markings comprising a pattern created using a pseudo random binary sequence or a de Bruijn sequence; and
transmitting by the control unit said control data to a multidirectional feedback device, wherein said multidirectional feedback device uses said control data to provide an operator with feedback to guide at least one of the handheld imaging device and the medical intervention tool toward the target, wherein the feedback further indicates deviation between the target location and the trajectory of the medical intervention tool.

16. The method of claim 15, wherein said multidirectional feedback device provides the feedback to the operator using at least one of: haptic display actuations, audio feedback, or visual feedback.

17. The method of claim 16, wherein the haptic display actuations comprise at least one of: torque impulses generated by one or more asymmetrical-impulse-driven flywheels or vibrotactile impulses generated by one or more asymmetric vibration actuators.

18. The method of claim 17, wherein at least one of the one or more asymmetrical-impulse-driven flywheels are oriented so as to be linearly independent and the at least one of the one or more asymmetric vibration actuators are oriented so as to be linearly independent.

19. The method of claim 16, wherein the haptic display actuations provide up to six degrees of freedom.

20. The method of claim 15, wherein the imaging device is a handheld ultrasound probe and the multidirectional feedback device is removably attached to the handheld ultrasound probe or integrated into the handheld ultrasound probe.

21. The method of claim 15, wherein the multidirectional feedback device includes one or more sensing devices comprising at least one of: an accelerometer, a gyroscope, a magnetometer, or optical sensors.

22. The method of claim 21, wherein said one or more sensing devices provide a relative pose between the multidirectional feedback device and the handheld imaging device and said method further comprises:
calculating a new pose deviation based on the pose deviation of the imaging device and the relative pose between the multidirectional feedback device and the imaging device.

23. The method of claim 15, wherein said feedback instructs the operator to continuously position the handheld imaging device along a time-varying path to provide multiple differing images of an area to produce a three-dimensional image of the area.

24. The method of claim 15, wherein the multidirectional feedback device provides the operator with feedback to continuously position the handheld imaging device within predefined operation pose boundaries, within updated operation pose boundaries that are updated during system operation, or within a combination of predefined operation pose boundaries and updated operation pose boundaries.

25. The method of claim 15, wherein the multidirectional feedback device is physically separate from the imaging device.

26. The method of claim 25, wherein the multidirectional feedback device is housed in a housing strapped on to a body part of the operator.

27. The method of claim 26, wherein the multidirectional feedback device is housed in a wrist-worn, finger-worn, or forehead-worn housing.

28. The method of claim 15, wherein the multidirectional feedback device provides the operator with feedback to continuously position the handheld imaging device along a time-varying path.

29. The method of claim 15, wherein the multidirectional feedback device provides the operator with feedback to continuously position the medical intervention tool within predefined operation pose boundaries, within updated operation pose boundaries that are updated during system operation, or within a combination of predefined operation pose boundaries and updated operation pose boundaries.

30. A method of guided navigation during a medical procedure, the method comprising:
   receiving by a control unit a target location;
   determining by the control unit an initial pose of a medical intervention tool;
   calculating by the control unit a pose deviation relative to said initial pose of the medical intervention tool;
   translating by the control unit said pose deviation into control data;
   obtaining by the control unit a trajectory of the medical intervention tool based on one or more detectable markings provided on the medical intervention tool, the one or more detectable markings comprising a pattern created using a pseudo random binary sequence or a de Bruijn sequence; and
   transmitting by the control unit said control data to a multidirectional feedback device, wherein said multidirectional feedback device uses said control data to provide an operator with feedback to guide the medical intervention tool toward the target, wherein the feedback further indicates deviation between the target location and the trajectory of the medical intervention tool.

* * * * *